United States Patent
Hall et al.

(10) Patent No.: US 8,417,350 B2
(45) Date of Patent: Apr. 9, 2013

(54) RECORDABLE MACROS FOR PACEMAKER FOLLOW-UP

(75) Inventors: Jeffrey A. Hall, Clanton, AL (US); G. Neal Kay, Birmingham, AL (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 13/618,914

(22) Filed: Sep. 14, 2012

(65) Prior Publication Data

US 2013/0013021 A1    Jan. 10, 2013

Related U.S. Application Data

(62) Division of application No. 11/467,466, filed on Aug. 25, 2006, now Pat. No. 8,280,518, which is a division of application No. 10/348,191, filed on Jan. 21, 2003, now Pat. No. 7,136,707.

(51) Int. Cl.
*A61N 1/00* (2006.01)

(52) U.S. Cl. .............. 607/59; 5/30; 5/32; 5/60

(58) Field of Classification Search .............. None
See application file for complete search history.

(56) References Cited

U.S. PATENT DOCUMENTS

| | | | |
|---|---|---|---|
| 4,432,360 A | 2/1984 | Mumford et al. | |
| 4,494,950 A | 1/1985 | Fischell | |
| 4,712,179 A | 12/1987 | Heimer | |
| 4,777,960 A | 10/1988 | Berger et al. | |
| 4,809,697 A | 3/1989 | Causey, III et al. | |
| 4,825,869 A | 5/1989 | Sasmor et al. | |
| 4,886,064 A | 12/1989 | Strandberg | |
| 4,928,688 A | 5/1990 | Mower | |
| 4,967,749 A | 11/1990 | Cohen | |
| 4,987,897 A | 1/1991 | Funke | |
| 5,031,629 A | 7/1991 | DeMarzo | |
| 5,097,831 A | 3/1992 | Lekholm | |
| 5,174,289 A | 12/1992 | Cohen | |
| 5,226,413 A | 7/1993 | Bennett et al. | |
| 5,251,626 A | 10/1993 | Nickolls et al. | |
| 5,267,560 A | 12/1993 | Cohen | |
| 5,282,838 A | 2/1994 | Hauser et al. | |
| 5,292,341 A | 3/1994 | Snell | |
| 5,321,618 A | 6/1994 | Gessman | |
| 5,372,607 A | 12/1994 | Stone et al. | |

(Continued)

FOREIGN PATENT DOCUMENTS

| | | |
|---|---|---|
| EP | 0297675 A1 | 1/1989 |
| EP | 0709058 A1 | 5/1996 |

(Continued)

OTHER PUBLICATIONS

"U.S. Appl. No. 09/738,407, Final Office Action mailed Jan. 14, 2003", 6 pgs.

(Continued)

*Primary Examiner* — Mark W Bockelman
(74) *Attorney, Agent, or Firm* — Schwegman Lundberg & Woessner, P.A.

(57) ABSTRACT

A device and method for programming an implantable pulse generator. In one embodiment, commands are entered designating implantable pulse generator programming variables into programmer memory. At least some of the commands are transformed into an executable macro. The macro is stored in the programmer memory. The macro is executed to transmit the programming variables to the implantable pulse generator.

20 Claims, 3 Drawing Sheets

U.S. PATENT DOCUMENTS

| | | | |
|---|---|---|---|
| 5,421,830 A | 6/1995 | Epstein et al. |
| 5,431,691 A | 7/1995 | Snell et al. |
| 5,441,047 A | 8/1995 | David et al. |
| 5,456,691 A | 10/1995 | Snell |
| 5,456,952 A | 10/1995 | Garza et al. |
| 5,487,752 A | 1/1996 | Salo et al. |
| 5,507,782 A | 4/1996 | Kieval et al. |
| 5,540,727 A | 7/1996 | Tockman et al. |
| 5,549,654 A | 8/1996 | Powell |
| 5,576,952 A | 11/1996 | Stutman et al. |
| 5,594,638 A | 1/1997 | Iliff |
| 5,607,460 A | 3/1997 | Kroll et al. |
| 5,630,835 A | 5/1997 | Brownlee |
| 5,662,691 A | 9/1997 | Behan et al. |
| 5,666,487 A | 9/1997 | Goodman et al. |
| 5,690,690 A | 11/1997 | Nappholz et al. |
| 5,693,076 A | 12/1997 | Kaemmerer |
| 5,697,959 A | 12/1997 | Poore |
| 5,713,937 A | 2/1998 | Nappholz et al. |
| 5,716,382 A | 2/1998 | Snell |
| 5,731,296 A | 3/1998 | Sollevi |
| 5,752,976 A | 5/1998 | Duffin et al. |
| 5,792,203 A | 8/1998 | Schroeppel |
| 5,800,473 A | 9/1998 | Faisandier |
| 5,817,137 A | 10/1998 | Kaemmerer |
| 5,833,623 A | 11/1998 | Mann et al. |
| 5,891,178 A | 4/1999 | Mann et al. |
| 5,911,132 A | 6/1999 | Sloane et al. |
| 5,935,060 A | 8/1999 | Iliff |
| 5,935,078 A | 8/1999 | Feierbach |
| 5,987,519 A | 11/1999 | Peifer et al. |
| 6,015,388 A | 1/2000 | Sackner et al. |
| 6,016,442 A | 1/2000 | Hsu et al. |
| 6,045,513 A | 4/2000 | Stone et al. |
| 6,070,101 A | 5/2000 | Struble et al. |
| 6,073,049 A | 6/2000 | Alt et al. |
| 6,076,015 A | 6/2000 | Hartley et al. |
| 6,081,786 A | 6/2000 | Barry et al. |
| 6,091,990 A | 7/2000 | Hsu et al. |
| 6,102,874 A | 8/2000 | Stone et al. |
| 6,112,224 A | 8/2000 | Peifer et al. |
| 6,129,744 A | 10/2000 | Boute |
| 6,141,586 A | 10/2000 | Mower |
| 6,144,880 A | 11/2000 | Ding et al. |
| 6,148,234 A | 11/2000 | Struble |
| 6,168,563 B1 | 1/2001 | Brown |
| 6,249,705 B1 | 6/2001 | Snell |
| 6,250,309 B1 | 6/2001 | Krichen et al. |
| 6,272,377 B1 | 8/2001 | Sweeney et al. |
| 6,280,389 B1 | 8/2001 | Ding et al. |
| 6,285,907 B1 | 9/2001 | Kramer et al. |
| 6,304,773 B1 | 10/2001 | Taylor et al. |
| 6,351,673 B1 | 2/2002 | Ding et al. |
| 6,351,675 B1 | 2/2002 | Tholen et al. |
| 6,360,127 B1 | 3/2002 | Ding et al. |
| 6,363,282 B1 | 3/2002 | Nichols et al. |
| 6,370,427 B1 | 4/2002 | Alt et al. |
| 6,400,982 B2 | 6/2002 | Sweeney et al. |
| 6,411,847 B1 | 6/2002 | Mower |
| 6,441,747 B1 | 8/2002 | Khair et al. |
| 6,442,432 B2 | 8/2002 | Lee |
| 6,442,433 B1 | 8/2002 | Linberg |
| 6,497,655 B1 | 12/2002 | Linberg et al. |
| 6,526,313 B2 | 2/2003 | Sweeney et al. |
| 6,542,775 B2 | 4/2003 | Ding et al. |
| RE38,119 E | 5/2003 | Mower |
| 6,564,104 B2 | 5/2003 | Nelson et al. |
| 6,597,951 B2 | 7/2003 | Kramer et al. |
| 6,622,040 B2 | 9/2003 | Ding et al. |
| 6,625,494 B2 | 9/2003 | Fang et al. |
| 6,665,558 B2 | 12/2003 | Kalgren et al. |
| 6,668,194 B2 | 12/2003 | VanHout |
| 6,669,631 B2 | 12/2003 | Norris et al. |
| 6,684,103 B2 | 1/2004 | Ding et al. |
| 6,687,547 B2 | 2/2004 | Goedeke et al. |
| 6,708,058 B2 | 3/2004 | Kim et al. |
| 6,735,479 B2 | 5/2004 | Fabian et al. |
| 6,804,555 B2 | 10/2004 | Warkentin |
| 6,804,558 B2 | 10/2004 | Haller et al. |
| 6,811,537 B2 | 11/2004 | Bardy |
| 6,856,836 B2 | 2/2005 | Ding et al. |
| 6,859,665 B2 | 2/2005 | Ding et al. |
| 6,878,112 B2 | 4/2005 | Linberg et al. |
| 6,915,160 B2 | 7/2005 | Auricchio et al. |
| 6,961,616 B2 | 11/2005 | Kramer et al. |
| 6,999,815 B2 | 2/2006 | Ding et al. |
| 7,003,349 B1 | 2/2006 | Andersson et al. |
| 7,013,176 B2 | 3/2006 | Ding et al. |
| 7,070,562 B2 | 7/2006 | Bardy |
| 7,110,817 B2 | 9/2006 | Yu et al. |
| 7,123,960 B2 | 10/2006 | Ding et al. |
| 7,136,707 B2 | 11/2006 | Hall et al. |
| 7,158,830 B2 | 1/2007 | Yu et al. |
| 7,181,285 B2 | 2/2007 | Lindh et al. |
| 7,184,835 B2 | 2/2007 | Kramer et al. |
| 7,203,540 B2 | 4/2007 | Ding et al. |
| 7,231,248 B2 | 6/2007 | Kramer et al. |
| 7,310,554 B2 | 12/2007 | Kramer et al. |
| 7,383,088 B2 | 6/2008 | Spinelli et al. |
| 7,532,924 B2 | 5/2009 | Ternes |
| 7,546,162 B2 | 6/2009 | Ding et al. |
| 7,630,764 B2 | 12/2009 | Ding et al. |
| 7,672,721 B2 | 3/2010 | Chirife et al. |
| 7,720,537 B2 | 5/2010 | Sheldon et al. |
| 7,769,449 B2 | 8/2010 | Chirife et al. |
| 7,899,533 B2 | 3/2011 | Chirife et al. |
| 7,899,534 B2 | 3/2011 | Lindh et al. |
| 8,099,165 B2 | 1/2012 | Lindh et al. |
| 8,280,518 B2 | 10/2012 | Hall et al. |
| 2001/0007053 A1 | 7/2001 | Bardy |
| 2001/0031997 A1 | 10/2001 | Lee |
| 2001/0039375 A1 | 11/2001 | Lee et al. |
| 2001/0039503 A1 | 11/2001 | Chan et al. |
| 2002/0016550 A1 | 2/2002 | Sweeney et al. |
| 2002/0019586 A1 | 2/2002 | Teller et al. |
| 2002/0023654 A1 | 2/2002 | Webb |
| 2002/0026103 A1 | 2/2002 | Norris et al. |
| 2002/0049482 A1 | 4/2002 | Fabian et al. |
| 2002/0120311 A1 | 8/2002 | Lindh et al. |
| 2002/0123672 A1 | 9/2002 | Christophersom et al. |
| 2003/0050803 A1 | 3/2003 | Marchosky |
| 2003/0088290 A1 | 5/2003 | Spinelli et al. |
| 2003/0171791 A1 | 9/2003 | KenKnight et al. |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0133080 A1 | 7/2004 | Mazar |
| 2004/0133246 A1 | 7/2004 | Ding et al. |
| 2004/0143304 A1 | 7/2004 | Hall et al. |
| 2006/0116727 A1 | 6/2006 | Ding et al. |
| 2006/0287692 A1 | 12/2006 | Hall et al. |
| 2007/0250125 A1 | 10/2007 | Lindh et al. |
| 2008/0027489 A1 | 1/2008 | Sheldon et al. |
| 2008/0077031 A1 | 3/2008 | Spinelli et al. |
| 2009/0005828 A1 | 1/2009 | Levine |
| 2009/0248104 A1 | 10/2009 | Ding et al. |
| 2010/0222840 A1 | 9/2010 | Chirife et al. |
| 2011/0022108 A1 | 1/2011 | Chirife et al. |
| 2011/0137368 A1 | 6/2011 | Lindh et al. |
| 2012/0004698 A1 | 1/2012 | Hopper et al. |
| 2012/0083854 A1 | 4/2012 | Lindh et al. |

FOREIGN PATENT DOCUMENTS

| | | |
|---|---|---|
| EP | 10066698 A2 | 1/2001 |
| WO | WO-9914882 A2 | 3/1999 |
| WO | WO-0041765 | 7/2000 |
| WO | WO-0041766 | 7/2000 |
| WO | WO-0167948 A2 | 9/2001 |

OTHER PUBLICATIONS

"U.S. Appl. No. 09/738,407, Non-Final Office Action mailed Aug. 23, 2002", 6 pgs.

"U.S. Appl. No. 09/738,407, Notice of Allowance mailed Apr. 7, 2003", 7 pgs.

"U.S. Appl. No. 09/738,407, Response filed Mar. 13, 2003 to Final Office Action mailed Jan. 14, 2003", 10 pgs.

"U.S. Appl. No. 09/738,407, Response filed Nov. 22, 2002 to Non-Final Office Action mailed Aug. 23, 2002", 7 pgs.

"U.S. Appl. No. 09/748,791, Response filed Aug. 13, 2004 to Advisory Action mailed Aug. 4, 2004", 1 pg.

"U.S. Appl. No. 10/008,354, Final Office Action mailed Jul. 12, 2006", 7 pgs.

"U.S. Appl. No. 10/008,354, Final Office Action mailed Jul. 19, 2007", 8 pgs.

"U.S. Appl. No. 10/008,354, Non Final office action mailed Jul. 1, 2004", 5 pgs.

"U.S. Appl. No. 10/008,354, Non-Final Office Action mailed Apr. 20, 2005", 8 pgs.

"U.S. Appl. No. 10/008,354, Non-Final Office Action mailed Sep. 27, 2006", 7 pgs.

"U.S. Appl. No. 10/008,354, Non-Final Office Action mailed Dec. 19, 2005", 9 pgs.

"U.S. Appl. No. 10/008,354, Notice of Allowance mailed Jan. 23, 2008", 4 pgs.

"U.S. Appl. No. 10/008,354, Notice of Allowance mailed Sep. 28, 2007", 4 pgs.

"U.S. Appl. No. 10/008,354, Response filed Jan. 3, 2005 to Non Final office action mailed Jul. 1, 2004", 13 pgs.

"U.S. Appl. No. 10/008,354, Response filed Feb. 27, 2007 to Non Final office action mailed Sep. 27, 2006", 17 pgs.

"U.S. Appl. No. 10/008,354, Response filed Mar. 20, 2006 to Non Final office action mailed Dec. 19, 2005", 13 pgs.

"U.S. Appl. No. 10/008,354, Response filed Aug. 30, 2005 to Non Final office action mailed Apr. 20, 2005", 12 pgs.

"U.S. Appl. No. 10/008,354, Response filed Sep. 12, 2006 to Final office action mailed Jul. 12, 2006", 13 pgs.

"U.S. Appl. No. 10/008,354, Response filed Sep. 19, 2007 to Final Office Action mailed Jul. 19, 2007", 15 pgs.

"U.S. Appl. No. 10/655,569, Non-Final Office Action mailed Mar. 28, 2005", 7 pgs.

"U.S. Appl. No. 10/655,569, Notice of Allowance mailed Aug. 25, 2005", 4 pgs.

"U.S. Appl. No. 10/655,569, Response and Supplemental Preliminary Amendment filed Mar. 4, 2005 to Restriction Requirement mailed Feb. 4, 2005", 12 pgs.

"U.S. Appl. No. 10/655,569, Response filed Jul. 28, 2005 to Non-Final Office Action mailed Mar. 28, 2005", 8 pgs.

"U.S. Appl. No. 10/655,569, Restriction Requirement mailed Feb. 4, 2005", 5 pgs.

"U.S. Appl. No. 11/276,007, Non-Final Office Action mailed Jun. 18, 2008", 10 pgs.

"U.S. Appl. No. 11/276,007, Notice of Allowance mailed Feb. 6, 2009", 5 pgs.

"U.S. Appl. No. 11/276,007, Preliminary Amendment filed Mar. 13, 2006", 3 pgs.

"U.S. Appl. No. 11/276,007, Response filed Oct. 20, 2008 to Non Final Office Action mailed Jun. 18, 2008", 8 pgs.

"U.S. Appl. No. 11/985,995, Examiner Interview Summary mailed Jan. 18, 2012", 3 pgs.

"U.S. Appl. No. 11/985,995, Final Office Action mailed Nov. 21, 2011", 12 pgs.

"U.S. Appl. No. 11/985,995, Non-Final Office Action mailed Mar. 8, 2011", 12 pgs.

"U.S. Appl. No. 11/985,995, Response filed May 21, 2012 to Final Office Action mailed Nov. 21, 2011", 12 pgs.

"U.S. Appl. No. 11/985,995, Response filed Sep. 7, 2011 to Non-Final Office Action mailed Mar. 8, 2011", 15 pgs.

"U.S. Appl. No. 12/480,485, Response to Restriction Requirement mailed Jun. 5, 2012", 8 pgs.

"U.S. Appl. No. 12/480,485, Restriction Requirement mailed Jun. 5, 2012", 5 pgs.

"U.S. Appl. No. 13/326,681, Non Final Office Action mailed Jul. 11, 2012", 10 pgs.

"U.S. Appl. No. 13/326,681, Notice of Allowance mailed Oct. 29, 2012", 6 pgs.

"U.S. Appl. No. 13/326,681, Response filed Oct. 5, 2012 to Non Final Office Action mailed Jul. 11, 2012", 13 pgs.

"Definition of Prescription", Webster's Third New International Dictionary, (c) 2002 Merriam-Webster, (2002), p. 1792.

"Landmark study finds high resting heart associated with shorter life expectancy", Medicine & Health/ Diseases http://www.physorg.com/news/2010-10-landmark-high-resting-heart-shorter.html, (Oct. 26, 2010), 2 pgs.

Abraham, W T, "Cardiac Resynchronization in Chronic Heart Failure", New England Journal of Medicine, 346(24), (Jul. 13, 2002), 1845-1853.

Auricchio, A., "Effect of Pacing Chamber and Atrioventricular Delay on Acute Systolic Function of Paced Patients With Congestive Heart Failure", Circulation, 99(23), (Jun. 15, 1999), 2993-3001.

Auricchio, A., et al., "Long-term clinical effect of hemodynamically optimized cardiac resynchronization therapy in patients with heart failure and ventricular conduction delay", J Am Coll Cardiol., 39, (Jun. 19, 2002), 2026-33.

Boriani, G., et al., "Randomized comparison of simultaneous biventricular stimulation versus optimized interventricular delay in cardiac resynchronization therapy", Am Heart J., 151(5), (May 2006), 1050-8.

Bristow, M. R, et al., "Cardiac-resynchronization therapy with or without an implantable defibrillator in advanced chronic heart failure", N Engl J Med., 350, (May 20, 2004), 2140-50.

De Lurgio, D. B., et al., "A comparison of cardiac resynchronization by sequential biventricular pacing and left ventricular pacing to simultaneous biventricular pacing: rationale and design of the Decrease-HF clinical trial", J Card Fail., 11, (Apr. 2005), 233-9.

Gold, M. R, et al., "A prospective comparison of AV delay programming methods for hemodynamic optimization during cardiac resynchronization therapy", J Cardiovasc Electrophysiol., 18(5), (May 2007), 490-6.

Hunt, S. A, "ACC/AHA 2005 guideline update for the diagnosis and management of chronic heart failure in the adult", J Am Coll Cardiol., 46(6), (Sep. 20, 2005), e1-82.

Ji, J., "An Ultraminiature CMOS Pressure Sensor for a Multiplexed Cardiovascular Catheter", IEEE Transactions on Electron Devices, vol. 39, No. 10, (Oct. 1992), pp. 2260-2267.

Kass, D. A, "Cardiac resynchronization therapy", J Cardiovasc Electrophysiol., 16(Suppl 1), (Sep. 2005), S35-41.

Kass, D. A., "Improved Left Ventricular Mechanics From Acute VDD Pacing in Patients With Dilated Cardiomyopathy and Ventricular Conduction Delay", Circulation, 99(12), (Mar. 30, 1999), 1567-1573.

Linde, C., et al., "Long-term benefits of biventricular pacing in congestive heart failure: results from the MUltisite STimulation in cardiomyopathy (MUSTIC) study", J Am Coll Cardiol., 40, (Jul. 3, 2002), 111-8.

Lozier, Luke R, et al., "System for Identifying Candidates for ICD Implantation", U.S. Appl. No. 10/438,261, filed May 14, 2003, 15 pgs.

Nelson, Chester G., et al., "Dynamic Bandwidth Monitor and Adjuster for Remote Communications with a Medical Device", U.S. Appl. No. 60/173,083, filed Dec. 24, 1999, 12 pgs.

Perego, G. B, et al., "Simultaneous vs. sequential biventricular pacing in dilated cardiomyopathy: an acute hemodynamic study", Eur J Heart Fail., 5(3), (Jun. 2003), 305-13.

Rao, R. K, et al., "Reduced ventricular volumes and improved systolic function with cardiac resynchronization therapy: a randomized trial comparing simultaneous biventricular pacing, sequential biventricular pacing, and left ventricular pacing", Circulation, 115(16), (Apr. 24, 2007), 2136-2144.

Saxon, L. A, et al., "Effects of long-term biventricular stimulation for resynchronization on echocardiographic measures of remodeling", Circulation, 105(11), (Mar. 19, 2002), 1304-10.

Sharma, A. D, et al., "Percent Right Ventricular Pacing Predicts Outcomes in the DAVID Trial", Heart Rhythm, 2(8), (2005), 830-834.

Sogaard, P., et al., "Sequential versus simultaneous biventricular resynchronization for severe heart failure: evaluation by tissue Doppler imaging", Circulation, 106(16), (Oct. 15, 2002), 2078-84.

Stellbrink, Christoph, "Impact of Cardiac Resynchronization Therapy Using Hemodynamically Optimized Pacing on Left Ventricular Remodeling in Patients With Congestive Heart Failure and Ventricular Conduction Disturbances", Journal of the American College of Cardiology, vol. 38, No. 7, (Dec. 2001), 1957-1965.

Van Gelder, B. M., et al., "Effect of optimizing the VV interval on left ventricular contractility in cardiac resynchronization therapy", Am J Cardiol., 93(12), (Jun. 15, 2004), 1500-3.

Vanderheyden, M., et al., "Tailored echocardiographic interventricular delay programming further optimizes left ventricular performance after cardiac resynchronization therapy", Heart Rhythm, 2(10), (Oct. 2005), 1066-72.

Whinnett, Z. I, et al., "Haemodynamic effects of changes in atrioventricular and interventricular delay in cardiac resynchronisation therapy show a consistent pattern: analysis of shape, magnitude and relative importance of atrioventricular and interventricular delay", Heart, 92(11), (Nov. 2006), 1628-34.

Yu, C. M, et al., "Tissue Doppler Echocardiographic Evidence of Reverse Remodeling and Improved Synchronicity by Simultaneously Delaying Regional Contraction After Biventricular Pacing Therapy in Heart Failure", Circulation, 105(4), (Jan. 29, 2002), 438-445.

Yu, Yinghong, et al., "Biventricular mechanical asynchrony predicts hemodynamic effects of uni- and biventricular pacing", Am J Physiol Heart Circ Physiol, vol. 285, (2003), H2788-H2796.

"U.S. Appl. No. 09/748,791, Advisory Action mailed Aug. 4, 2004", 3 pgs.

"U.S. Appl. No. 09/748,791, Final Office Action mailed Mar. 9, 2004", 6 pgs.

"U.S. Appl. No. 09/748,791, Final Office Action mailed Aug. 23, 2005", 6 pgs.

"U.S. Appl. No. 09/748,791, Non-Final Office Action mailed Feb. 3, 2005", 6 pgs.

"U.S. Appl. No. 09/748,791, Non-Final Office Action mailed Feb. 10, 2006", 9 pgs.

"U.S. Appl. No. 09/748,791, Non-Final Office Action mailed Feb. 21, 2003", 9 pgs.

"U.S. Appl. No. 09/748,791, Non-Final Office Action mailed Aug. 28, 2002", 7 pgs.

"U.S. Appl. No. 09/748,791, Non-Final Office Action mailed Sep. 17, 2003", 8 pgs.

"U.S. Appl. No. 09/748,791, Notice of Allowance mailed Sep. 3, 2004", 7 pgs.

"U.S. Appl. No. 09/748,791, Notice of Allowance mailed Sep. 20, 2006", 5 pgs.

"U.S. Appl. No. 09/748,791, Preliminary Amendment filed Feb. 21, 2001", 2 pgs.

"U.S. Appl. No. 09/748,791, Response filed May 10, 2006 to Non Final Office Action mailed Feb. 10, 2006", 8 pgs.

"U.S. Appl. No. 09/748,791, Response filed Jul. 5, 2005 to Non Final Office Action mailed Feb. 3, 2005", 7 pgs.

"U.S. Appl. No. 09/748,791, Response filed Jul. 9, 2004 to Final Office Action mailed Mar. 9, 2004", 11 pgs.

"U.S. Appl. No. 09/748,791, Response filed Jul. 21, 2003 to Non Final Office Action mailed Feb. 21, 2003", 15 pgs.

"U.S. Appl. No. 09/748,791, Response filed Nov. 23, 2005 to Final Office Action mailed Aug. 23, 2005", 7 pgs.

"U.S. Appl. No. 09/748,791, Response filed Nov. 25, 2002 to Non Final Office Action mailed Aug. 28, 2002", 7 pgs.

"U.S. Appl. No. 09/748,791, Response filed Dec. 17, 2003 to Non Final Office Action mailed Sep. 17, 2003", 10 pgs.

"U.S. Appl. No. 11/467,466, Examiner Interview Summary mailed Jun. 27, 2012", 3 pgs.

"U.S. Appl. No. 11/467,466, Final Office Action mailed Jan. 24, 2011", 7 pgs.

"U.S. Appl. No. 11/467,466, Non Final Office Action mailed Apr. 4, 2011", 7 pgs.

"U.S. Appl. No. 11/467,466, Non Final Office Action mailed Aug. 6, 2010", 6 pgs.

"U.S. Appl. No. 11/467,466, Notice of Allowance mailed Jun. 12, 2012", 5 pgs.

"U.S. Appl. No. 11/467,466, Response filed Mar. 21, 2011 to Final Office Action mailed Jan. 24, 2011", 9 pgs.

"U.S. Appl. No. 11/467,466, Response filed May 17, 2010 to Restriction Requirement mailed Mar. 29, 2010", 9 pgs.

"U.S. Appl. No. 11/467,466, Response filed Jun. 28, 2011 to Non-Final Office Action mailed Apr. 4, 2011", 9 pgs.

"U.S. Appl. No. 11/467,466, Response filed Nov. 5, 2010 to Non Final Office Action mailed Aug. 6, 2010", 9 pgs.

"U.S. Appl. No. 11/467,466, Response filed Dec. 21, 2011 to Final Office Action mailed Sep. 26, 2011", 9 pgs.

"U.S. Appl. No. 11/467,466, Restriction Requirement mailed Mar. 29, 2010", 9 pgs.

"U.S. Appl. No. 11/476,466, Final Office Action mailed Sep. 26, 2011", 7 pgs.

"U.S. Appl. No. 11/624,035, Notice of Allowance mailed Oct. 25, 2010", 9 pgs.

"U.S. Appl. No. 13/027,681, Non-Final Office Action mailed May 26, 2011", 8 pgs.

"U.S. Appl. No. 13/027,681, Notice of Allowance mailed Sep. 22, 2011", 6 pgs.

"U.S. Appl. No. 13/027,681, Response filed Aug. 26, 2011 to Non-Final Office Action mailed May 26, 2011", 13 pgs.

"U.S. Appl. No. 11/467,466, Ex Parte Quayle Action mailed Apr. 5, 2012", 4 pgs.

Hall, Jeffrey A., et al., "Recordable Macros for Pacemaker Follow-Up", U.S. Appl. No. 10/348,191, filed Jan. 21, 2003, 17 pgs.

Lindh, Par, et al., "Expert System and Method", U.S. Appl. No. 09/748,791, filed Dec. 26, 2000, 45 pgs.

Mower, Morton, "Method and Apparatus for Treating Hemodynamic Disfunction", U.S. Patent Office Patent Application Information Retrieval (PAIR) search results for U.S. Appl. No. 10/214,474, filed Aug. 8, 2002, entitled, 3 pgs.

US 6,527,714, 03/2003, Bardy (withdrawn)

RECORDABLE MACROS FOR PACEMAKER FOLLOW-UP

PRIORITY

This application is a Division of U.S. application Ser. No. 11/467,466, filed on Aug. 25, 2006, which is a Division of U.S. application Ser. No. 10/348,191, filed on Jan. 21, 2003, now issued as U.S. Pat. No. 7,136,707, which are incorporated herein by reference in their entirety.

FIELD OF THE INVENTION

This document relates to systems implantable in a patient to treat cardiac arrhythmia, and in particular, to a programming device and method for using software or firmware macro-functions (hereinafter macros) to record a physician's programming preferences and procedural test order to partly automate follow-up procedures after a pacemaker, defibrillator, or any other device capable of diagnosing and treating cardiac arrhythmia has been implanted in a patient.

BACKGROUND

External programmers are used to non-invasively change the performance parameters of an implanted device such as a pacemaker or defibrillator. As the implantable devices become more sophisticated and are designed with more programmable features, it is advantageous to reduce the time necessary for physicians to change programming preferences for the implanted devices. Current methods require the operator of a programmer for an implanted device to re-enter a set of programmed parameters for the implanted device at the start of a follow-up procedure. This set of parameters may be defined by physician preferences or by settings needed to perform a test. The re-entry of programmed settings results in extra time needed to program the implanted device to overwrite default settings or perform a set of tests. What is needed is a programming device and method to automatically pre-load the set of parameters in the programming device to minimize the time necessary to reprogram the settings of the implanted device.

SUMMARY OF THE INVENTION

This document discusses a device and method for programming an implantable pulse generator. The programming device for an implantable pulse generator comprises a programmer memory, data entry means to enter implantable pulse generator programming variables into the programmer memory, a processor to transform the entry of programming variables into an executable macro as the variables are entered and storing the macro in the programmer memory, and a communication module to transmit the programming variables to the pulse generator when the processor executes the macro.

One embodiment of a method of programming an implantable pulse generator comprises entering commands designating implantable pulse generator programming variables into programmer memory, transforming at least some of the commands into an executable macro, storing the macro in the programmer memory, and executing the macro to transmit the programming variables to the implantable pulse generator. Another embodiment of a method of programming an implantable pulse generator comprises receiving data identifying the implantable pulse generator by an external programming device, loading a script file previously stored according to the identifying data into memory of the programming device, executing the script file to pre-load programming variables into the memory of a programming device, and selectively transmitting the programming variables via telemetry from the programming device to the implantable pulse generator for storage in memory of the implantable pulse generator.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, where like numerals refer to like components throughout the several views.

DETAILED DESCRIPTION

In the following detailed description, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Figure 1:
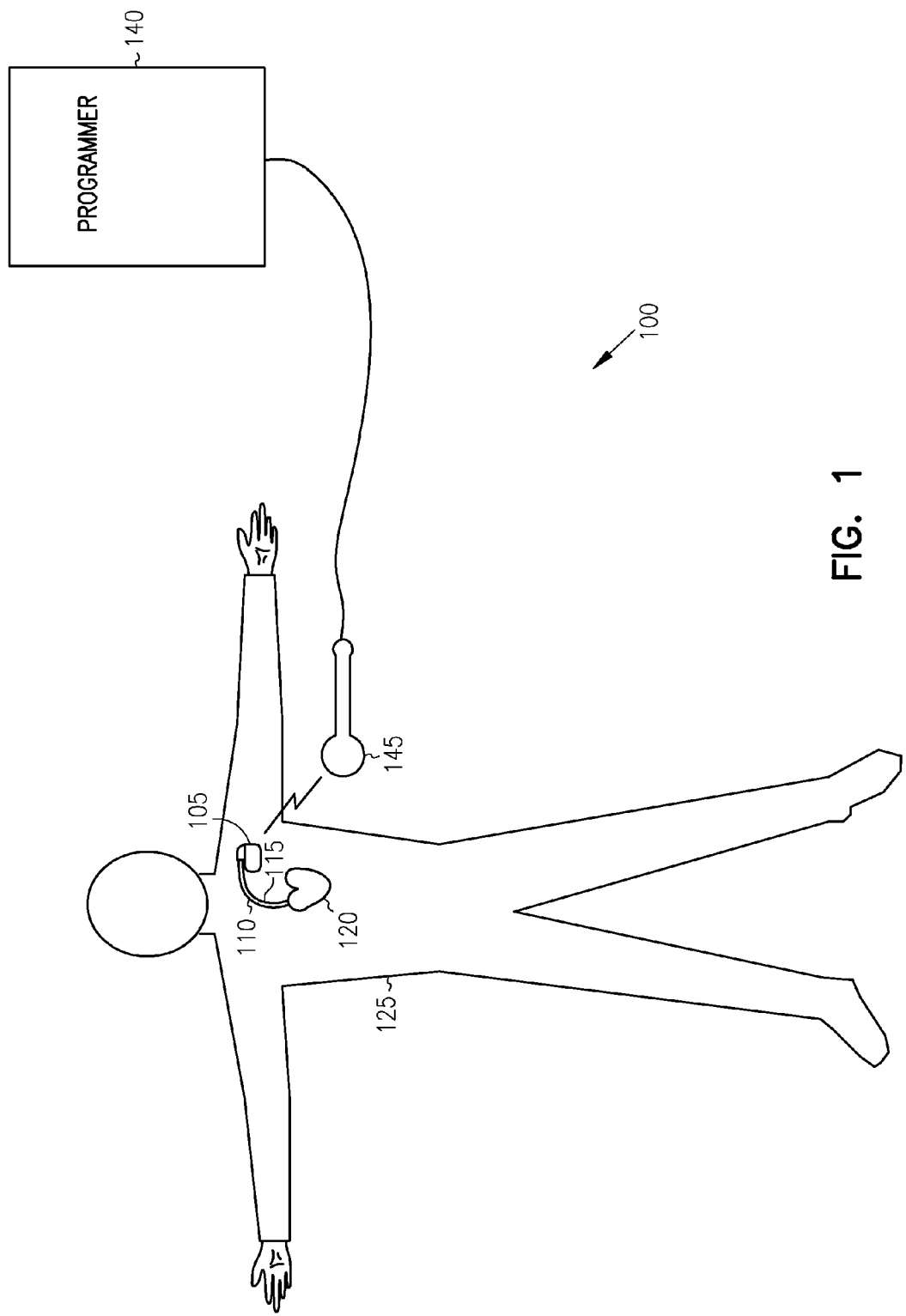
FIG. 1 shows one embodiment of a system to treat cardiac arrhythmia and an environment in which it is used.

FIG. 1 shows one embodiment of portions of a system 100 to treat cardiac arrhythmia. System 100 includes an implantable pulse generator (PG) 105 that is connected by a first cardiac lead 110 and a second cardiac lead 115, or one or more additional leads, to a heart 120 of a patient 125. Implantable PG 105 can take the form of a pacemaker, a defibrillator, or a cardioverter/defibrillator that includes pacing capability. System 100 also includes an external programming device, or programmer, 140 that provides for wireless communication with the implantable PG 105 using telemetry antenna 145. The external programmer transmits the programming variables to the implantable PG. The programming variables determine what therapy will be used to treat heart arrhythmias. The external programmer also receives information such as device serial numbers from the implantable PG 105.

Figure 2:
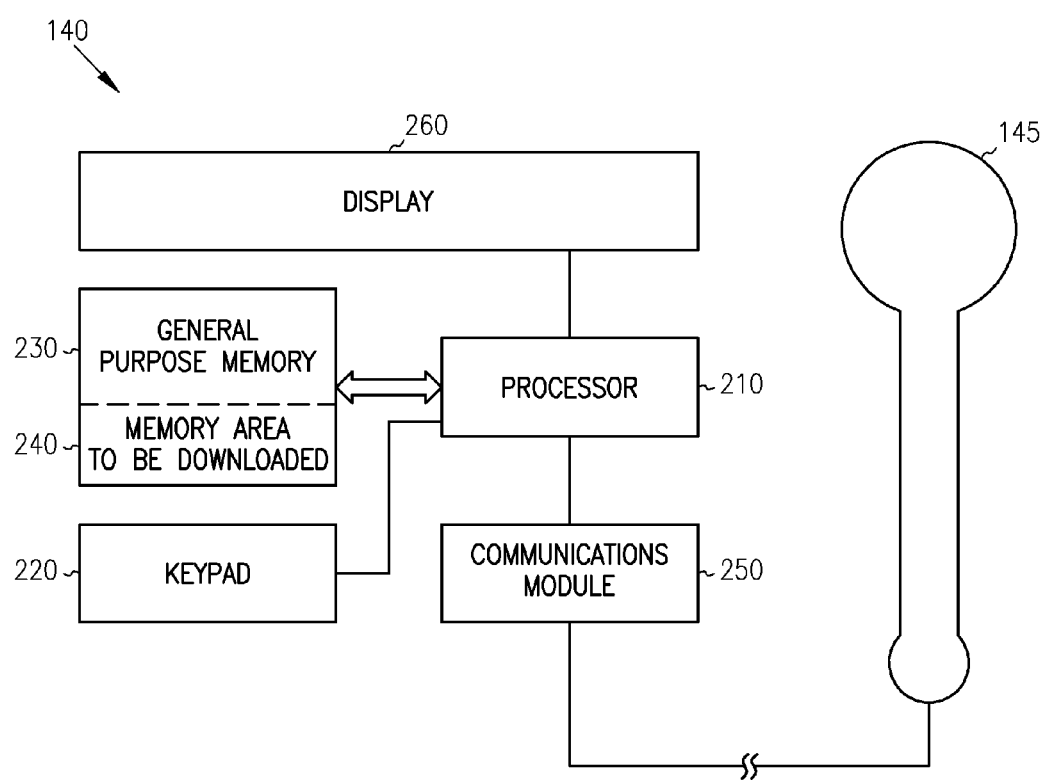
FIG. 2 is a block diagram of the components of an external programming device for an implantable device.

FIG. 2 is a block diagram of a programmer 140 for the implanted device. An operator enters programming variables by data entry means 220 into a memory 240 local to the external programmer 140 for transmitting to an implantable PG 105. The programming variables are shown to the operator by programmer display 260. In one embodiment, data entry means 220 is a keypad. In another embodiment, data entry means 220 is a computer mouse. In a further embodiment, the data entry means 220 is a drop-down menu and a computer mouse or a touch-screen display. In a further embodiment, data entry means 220 is a virtual keyboard which may be part of the programmer display 260. Processor 210 transforms the data entries of an operator into general memory 230 as a software or firmware macro. In one embodiment, memory 230 is a local hard drive for the programmer. In another embodiment, memory 230 is a diskette inserted into a local floppy disk drive. In an embodiment concerning the software of the programmer, the processor runs a software program such as VisualBasic™ (for a MS Windows based programmer) or QNX™ programming script (for QNX based programmers), or a program residing in firmware to record the macro.

The programmer then transmits the programming variables to the implantable PG 105 using communication module 250 and telemetry antenna 145. In one embodiment, the set of programming variables to be transmitted to the implantable PG 105 is defined by the device feature set of the type of implantable device. In another embodiment, the set of programming variables is defined by the cardiac disorder that afflicts the patient. In a further embodiment, the set of programming variables to be transmitted to the implantable PG 105 is checked to prevent overwriting a protected area of memory in the implanted device. In yet a further embodiment, the set of programming variables re-entered for downloading to the implantable PG 105 is checked to determine if the variable is appropriate for the implanted system. For example, the operator may try to download a pacing parameter for a pacing vector that is not implemented in the device. In subsequent programming sessions, processor 210 plays back the macro to either directly transmit the variables to the PG 105, or to pre-load the programming variables into local programmer memory 240 before selectively transmitting the variables to the PG 105.

Figure 3:
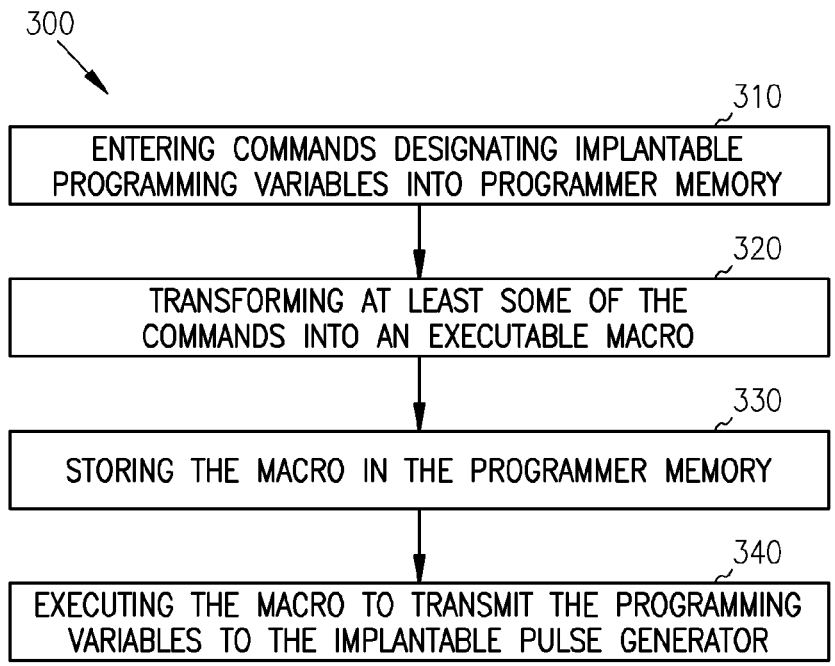
FIG. 3 is a flow chart showing one embodiment of a method of programming an implantable device using macros.

FIG. 3 is a flow chart showing one embodiment of a method 300 of programming an implanted device using macros. At 310 commands are entered designating implantable programmer variables into programmer memory. In one example of the embodiment, commands are entered by a programmer operator using a keypad. In another embodiment, a programmer operator enters programming variables into fields of the display 260. At 320 at least some of the commands are transformed into an executable macro. In one embodiment, commands are transformed by processor 210 recording the keystrokes of a programmer operator when the operator enters commands using a keypad. In another embodiment, the processor records a series of data values entered into fields of display 260. At 330, the executable macro is stored into programmer memory 230. At 340, the macro is executed to transmit the programming variables to the implantable PG 105.

In one embodiment, the macro pre-loads physician setting preferences to overwrite the default factory settings; especially in the area of electrophysiological testing, anti-tachycardia pacing (ATP), and other programmed stimulation.

In another embodiment, data identifying the implantable PG 105, such as the device serial number for example, is uploaded from the implantable PG 105, and the macro pre-loads variables required to conduct patient-testing of the device. In this manner, an entire set of tests is pre-programmed by replaying macros. The test results and programmed parameters are extracted from the external programmer 140 and inserted into a post-session follow-up communication. One embodiment of the communication is a predefined physician follow-up letter using, for example, additional macros written in Visual Basic™ for use in a word processing program such as MS Word™. Often a transfer of information between two different operating systems (OS) such as QNX™ (OS for the programmer) and MS Windows™ (OS for the computer generating physician follow-up letters) is performed through creation of a diskette with appropriate ANSI values to be imported into the word processing program such as MS Word™ or Word Perfect™

Figure 4:
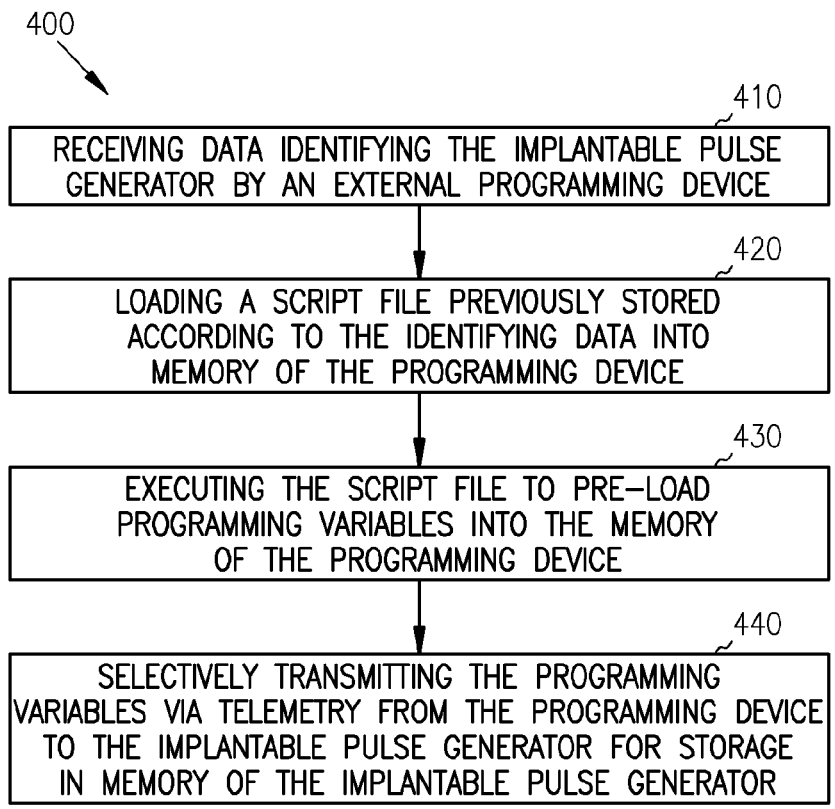
FIG. 4 is a flow chart showing one embodiment of a method of programming an implantable device using a previously stored script file.

FIG. 4 is a flow chart showing one embodiment of a method 400 of programming an implanted device using a previously stored script file. A script file is a text file written in a software language such as Visual Basic™ containing a sequence of executable commands. At step 410 the external programming device 140 receives data identifying the implantable PG 105. At step 420, the programming device 140 then loads a script file previously stored according to the identifying data into memory 230 of the programming device 140. In one embodiment, the programming device 140 displays a menu of script files associated with the implantable PG 105. In one example of associating the menus with the implantable PG 105, the menu displays the script files available for the model of PG 105. In another example, the menu displays the script files available for the cardiac disorder treated with the PG 105. In a further example, the menu displays the script files available for different cardiac disorders that require specific device programming of the PG 105.

In another embodiment, the script file menus are associated with the device programming preferences of a physician. In one example, the script file menus are associated with a physician's preferences for the model of the PG 105. In another example, the script file menus are associated with a physician's preferences for a set of tests to execute based on the cardiac disorder. At step 430, the script file chosen by the operator from a menu is executed to pre-load programming variables into local memory 240 of programming device 140. At step 440, the programming variables are selectively transmitted via telemetry from the programming device 140 to the implantable pulse generator for storage in memory of the implantable PG 105. In one embodiment of selectively transmitting the programming variables, the script file either transmits the variables via telemetry to the PG 105 by the operator without modification, or the variables are transmitted after review and minor changes are made by the operator.

Although specific examples have been illustrated and described herein, it will be appreciated by those of ordinary skill in the art that any other embodiment that exists that is calculated to achieve the same purpose may be substituted for the specific example shown. This application is intended to cover any adaptations or variations of the present invention. Therefore, it is intended that this invention be limited only by the claims and their equivalents.

What is claimed is:

1. A computer readable media including instructions for performing the method comprising:
    receiving data identifying the implantable pulse generator by an external programming device;
    loading a script file previously stored according to the identifying data into memory of the programming device, wherein loading a script file includes presenting a script file according to a cardiac disorder in which modification of at least one programming parameter of the implantable pulse generator is needed to treat the cardiac disorder;
    executing the script file to:
        pre-load programming variables into the memory of a programming device; and
        present at least a portion of the programming variables on a display for modification, if any, by an operator;
    checking any modified programming variables to determine if the modification is appropriate for the implantable pulse generator; and
    selectively transmitting the programming variables via telemetry from the programming device to the implantable pulse generator for storage in memory of the implantable pulse generator.

2. A programmer for programming an implantable pulse generator comprising:
  a programmer memory to store a plurality of script files, each script file containing a sequence of executable commands to program an implantable pulse generator;
  data receiving means to receive data identifying an implantable pulse generator to be programmed;
  a display adapted to display a menu of stored script files associated with the implantable pulse generator, and display at least a portion of a script file;
  data receiving means to receive modifications, if any, to the script file;
  a processor coupled to the memory, the processor adapted to:
    display a script file according to a cardiac disorder in which modification of at least one programming parameter of the implantable pulse generator is needed to treat the cardiac disorder;
    execute the script file to:
      automatically pre-load programming variables of the implantable pulse generator; and
      display at least a portion of the programming variables for modification, if any, by an operator; and
    check any modified programming variables to determine if the modification is appropriate for the implantable pulse generator; and
  a communication module coupled to the processor to transmit the programming variables via telemetry to the pulse generator when the processor executes the script file.

3. The programmer of claim 2, wherein the display is adapted to display the script files according to an implantable pulse generator model.

4. The programmer of claim 2, wherein the display is adapted to display the script files available for the cardiac disorder treatable with the implantable pulse generator.

5. The programmer of claim 2, wherein the display is adapted to display the script files available for different cardiac disorders that require specific device programming of the implantable pulse generator.

6. The programmer of claim 2, wherein the display is adapted to display the script files according to the programming preferences of a physician.

7. The programmer of claim 2, wherein the display is adapted to display the script files according to a physician's programming preferences for the model of the implantable pulse generator.

8. The programmer of claim 2, wherein the display is adapted to display the script files according to a physician's programming preferences for a set of tests to execute based on a cardiac disorder.

9. The programmer of claim 2, wherein the display is adapted to display a script file that is particularized to programmable features of the identified implantable pulse generator.

10. The programmer of claim 2, wherein the processor is adapted to display one or more script files for the identified implantable pulse generator model that are particularized to a preference of a physician.

11. The programmer of claim 2, wherein the processor is adapted to display one or more script files for a cardiac disorder, wherein the one or more script files are particularized to a preference of a physician.

12. The programmer of claim 11, wherein the processor is adapted to display the one or more script files in an order particularized to a preference of the physician.

13. The programmer of claim 2, wherein the processor is adapted to pre-load a script file particularized to one of a plurality of tests to be performed.

14. The programmer of claim 2, wherein the processor is adapted to pre-load a script file containing a plurality of tests in an order that is particularized to a preference of a physician.

15. The programmer of claim 14, wherein the processor is adapted to pre-load a script file particularized to program the implantable pulse generator for an in vivo electrophysiological test.

16. The programmer of claim 2, wherein the processor is adapted to:
  pre-load a script file that includes programming variables particularized to perform a patient test;
  execute the script file to program the implantable pulse generator with the programming variables; and
  insert results of the patient test into a post-session follow-up communication.

17. The programmer of claim 16, wherein the communication module is adapted to receive measured test data from the implantable pulse generator indicative of the results of the patient test and to insert that measured test data in the post-session follow-up communication.

18. The programmer of claim 2, wherein the receiving means to receive data identifying an implantable pulse generator includes the communication module adapted to upload the identifying data from the implantable pulse generator.

19. The programmer of claim 2, wherein the processor is adapted to check whether transmitting the programming variables would overwrite a protected area of memory in the identified implantable medical device.

20. The programmer of claim 2, wherein the processor is adapted to display one or more script files that are particularized to a preference of a physician for programming the implantable pulse generator for anti-tachycardia pacing (ATP) therapy.

* * * * *